US008776792B2

(12) United States Patent
Milne (10) Patent No.: US 8,776,792 B2
(45) Date of Patent: Jul. 15, 2014

(54) METHODS AND SYSTEMS FOR VOLUME-TARGETED MINIMUM PRESSURE-CONTROL VENTILATION

(75) Inventor: Gary Milne, Louisville, CO (US)

(73) Assignee: Covidien LP, Mansfield, MA (US)

( * ) Notice: Subject to any disclaimer, the term of this patent is extended or adjusted under 35 U.S.C. 154(b) by 347 days.

(21) Appl. No.: 13/098,066

(22) Filed: Apr. 29, 2011

(65) Prior Publication Data
US 2012/0272960 A1 Nov. 1, 2012

(51) Int. Cl.
*A61M 16/00* (2006.01)
*A62B 7/00* (2006.01)

(52) U.S. Cl.
USPC ............. 128/204.21; 128/204.18; 128/204.23

(58) Field of Classification Search
USPC ............. 128/204.18, 204.21–204.23, 204.26
See application file for complete search history.

(56) References Cited

U.S. PATENT DOCUMENTS

| | | | |
|---|---|---|---|
| 4,127,123 A | 11/1978 | Bird | |
| 4,448,192 A | 5/1984 | Stawitcke et al. | |
| 4,527,557 A | 7/1985 | DeVries et al. | |
| 4,637,385 A | 1/1987 | Rusz | |
| 4,655,213 A | 4/1987 | Rapoport et al. | |
| 4,752,089 A | 6/1988 | Carter | |
| 4,773,411 A | 9/1988 | Downs | |
| 4,805,612 A | 2/1989 | Jensen | |
| 4,805,613 A | 2/1989 | Bird | |
| 4,821,709 A | 4/1989 | Jensen | |
| 4,921,642 A | 5/1990 | LaTorraca | |
| 4,954,799 A | 9/1990 | Kumar | |
| 4,986,268 A | 1/1991 | Tehrani | |
| 5,044,362 A | 9/1991 | Younes | |
| 5,057,822 A | 10/1991 | Hoffman | |
| 5,072,737 A | 12/1991 | Goulding | |
| 5,107,830 A | 4/1992 | Younes | |
| 5,148,802 A | 9/1992 | Sanders et al. | |
| 5,150,291 A | 9/1992 | Cummings et al. | |
| 5,161,525 A * | 11/1992 | Kimm et al. ............ | 128/204.26 |
| 5,165,398 A | 11/1992 | Bird | |
| 5,237,987 A | 8/1993 | Anderson et al. | |
| 5,239,995 A | 8/1993 | Estes et al. | |
| 5,271,389 A | 12/1993 | Isaza et al. | |
| 5,279,549 A | 1/1994 | Ranford | |
| 5,299,568 A | 4/1994 | Forare et al. | |

(Continued)

FOREIGN PATENT DOCUMENTS

EP 0858352 1/2005
EP 0982043 5/2007

(Continued)

OTHER PUBLICATIONS

7200 Series Ventilator, Options, and Accessories: Operator's Manual. Nellcor Puritan Bennett, Part No. 22300 A, Sep. 1990.

(Continued)

*Primary Examiner* — Justine Yu
*Assistant Examiner* — Douglas Sul (57) ABSTRACT

The systems and methods include providing a volume-targeted minimum pressure-control breath type during ventilation of a patient. The system and methods provide a novel breath type that allows an operator to input a tidal volume and receive some of the benefits of utilizing an airway pressure release ventilation (APRV) breath type in combination with some of the benefits of utilizing a volume-targeted-pressure-control (VC+) breath type.

17 Claims, 3 Drawing Sheets

(56) References Cited

U.S. PATENT DOCUMENTS

| | | |
|---|---|---|
| 5,301,921 A | 4/1994 | Kumar |
| 5,307,795 A | 5/1994 | Whitwam et al. |
| 5,313,937 A | 5/1994 | Zdrojkowski |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,353,788 A | 10/1994 | Miles |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,388,575 A | 2/1995 | Taube |
| 5,390,666 A | 2/1995 | Kimm et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,452,714 A | 9/1995 | Anderson et al. |
| 5,474,062 A | 12/1995 | DeVires et al. |
| 5,492,113 A | 2/1996 | Estes et al. |
| 5,494,028 A | 2/1996 | DeVries et al. |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,220 A | 7/1996 | Gropper et al. |
| 5,542,415 A | 8/1996 | Brody |
| 5,544,674 A | 8/1996 | Kelly |
| 5,549,106 A | 8/1996 | Gruenke et al. |
| 5,551,418 A | 9/1996 | Estes et al. |
| 5,551,419 A | 9/1996 | Froehlich et al. |
| 5,555,880 A | 9/1996 | Winter et al. |
| 5,572,993 A | 11/1996 | Kurome et al. |
| 5,575,283 A | 11/1996 | Sjoestrand |
| 5,582,163 A | 12/1996 | Bonassa |
| 5,596,984 A | 1/1997 | O'Mahoney et al. |
| 5,598,838 A | 2/1997 | Servidio et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,682,878 A | 11/1997 | Ogden |
| 5,692,497 A | 12/1997 | Schnitzer et al. |
| 5,694,923 A | 12/1997 | Hete et al. |
| 5,715,812 A | 2/1998 | Deighan et al. |
| 5,735,267 A | 4/1998 | Tobia |
| 5,743,253 A | 4/1998 | Castor et al. |
| 5,752,506 A | 5/1998 | Richardson |
| 5,752,509 A | 5/1998 | Lachmann et al. |
| 5,762,480 A | 6/1998 | Adahan |
| 5,765,558 A | 6/1998 | Psaros et al. |
| 5,769,082 A | 6/1998 | Perel |
| 5,771,884 A | 6/1998 | Yarnall et al. |
| 5,782,233 A | 7/1998 | Niemi et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lall |
| 5,829,441 A | 11/1998 | Kidd et al. |
| 5,864,938 A | 2/1999 | Gansel et al. |
| 5,865,168 A | 2/1999 | Isaza |
| 5,865,173 A | 2/1999 | Froehlich |
| 5,868,133 A | 2/1999 | DeVries et al. |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,891,023 A | 4/1999 | Lynn |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,381 A | 6/1999 | Nord |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,931,162 A | 8/1999 | Christian |
| 5,934,274 A | 8/1999 | Merrick et al. |
| 5,937,853 A | 8/1999 | Strom |
| 5,957,130 A | 9/1999 | Krahbichler et al. |
| 5,970,975 A | 10/1999 | Estes et al. |
| 5,975,081 A | 11/1999 | Hood et al. |
| 6,000,396 A | 12/1999 | Melker et al. |
| 6,015,388 A | 1/2000 | Sackner et al. |
| 6,024,089 A | 2/2000 | Wallace et al. |
| 6,029,664 A | 2/2000 | Zdrojkowski et al. |
| 6,041,777 A | 3/2000 | Faithfull et al. |
| 6,041,780 A * | 3/2000 | Richard et al. ........... 128/204.18 |
| 6,047,860 A | 4/2000 | Sanders |
| 6,076,523 A | 6/2000 | Jones et al. |
| 6,099,481 A | 8/2000 | Daniels et al. |
| 6,105,575 A | 8/2000 | Estes et al. |
| 6,116,240 A | 9/2000 | Merrick et al. |
| 6,116,464 A | 9/2000 | Sanders |
| 6,123,072 A | 9/2000 | Downs |
| 6,123,073 A | 9/2000 | Schlawin et al. |
| 6,131,571 A | 10/2000 | Lampotang et al. |
| 6,135,105 A | 10/2000 | Lampotang et al. |
| 6,135,106 A | 10/2000 | Dirks et al. |
| 6,142,150 A | 11/2000 | O'Mahony et al. |
| 6,148,814 A | 11/2000 | Clemmer et al. |
| 6,152,129 A | 11/2000 | Berthon-Jones |
| 6,158,432 A | 12/2000 | Biondi et al. |
| 6,161,539 A | 12/2000 | Winter |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,220,245 B1 | 4/2001 | Takabayashi et al. |
| 6,240,920 B1 | 6/2001 | Strom |
| 6,253,765 B1 | 7/2001 | Hognelid et al. |
| 6,257,234 B1 | 7/2001 | Sun |
| 6,269,812 B1 | 8/2001 | Wallace et al. |
| 6,273,088 B1 | 8/2001 | Hillsman |
| 6,273,444 B1 | 8/2001 | Power |
| 6,279,569 B1 | 8/2001 | Berthon-Jones |
| 6,283,119 B1 | 9/2001 | Bourdon |
| 6,302,105 B1 | 10/2001 | Wickham et al. |
| 6,302,851 B1 | 10/2001 | Gedeon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,308,706 B1 | 10/2001 | Lammers et al. |
| 6,321,748 B1 | 11/2001 | O'Mahoney |
| 6,325,785 B1 | 12/2001 | Babkes et al. |
| 6,345,619 B1 | 2/2002 | Finn |
| 6,349,724 B1 | 2/2002 | Burton et al. |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,390,091 B1 | 5/2002 | Banner et al. |
| 6,401,713 B1 | 6/2002 | Hill et al. |
| 6,412,483 B1 | 7/2002 | Jones et al. |
| 6,427,689 B1 | 8/2002 | Estes et al. |

(56) References Cited

U.S. PATENT DOCUMENTS

| | | |
|---|---|---|
| 6,431,169 B1 | 8/2002 | do Val et al. |
| 6,439,229 B1 | 8/2002 | Du et al. |
| 6,463,930 B2 | 10/2002 | Biondi et al. |
| 6,467,477 B1 | 10/2002 | Frank et al. |
| 6,467,478 B1 | 10/2002 | Merrick et al. |
| 6,484,719 B1 | 11/2002 | Berthon-Jones |
| 6,526,970 B2 | 3/2003 | DeVries et al. |
| 6,530,372 B1 | 3/2003 | Madaus et al. |
| 6,532,956 B2 | 3/2003 | Hill |
| 6,532,957 B2 | 3/2003 | Berthon-Jones |
| 6,532,960 B1 | 3/2003 | Yurko |
| 6,533,730 B2 | 3/2003 | Strom |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,568,387 B2 | 5/2003 | Davenport et al. |
| 6,571,795 B2 | 6/2003 | Bourdon |
| 6,575,163 B1 | 6/2003 | Berthon-Jones |
| 6,581,595 B1 | 6/2003 | Murdock et al. |
| 6,581,597 B2 | 6/2003 | Sugiura |
| 6,584,973 B1 * | 7/2003 | Biondi et al. ............ 128/204.21 |
| 6,595,213 B2 | 7/2003 | Bennarsten |
| 6,609,517 B1 | 8/2003 | Estes et al. |
| 6,612,995 B2 | 9/2003 | Leonhardt et al. |
| 6,622,726 B1 | 9/2003 | Du |
| 6,629,527 B1 | 10/2003 | Estes et al. |
| 6,629,934 B2 | 10/2003 | Mault et al. |
| 6,640,806 B2 | 11/2003 | Yurko |
| 6,644,310 B1 | 11/2003 | Delache et al. |
| 6,644,312 B2 | 11/2003 | Berthon-Jones et al. |
| 6,647,984 B1 | 11/2003 | O'Dea |
| 6,659,101 B2 | 12/2003 | Berthon-Jones |
| 6,668,824 B1 | 12/2003 | Isaza et al. |
| 6,668,829 B2 | 12/2003 | Biondi et al. |
| 6,675,801 B2 | 1/2004 | Wallace et al. |
| 6,679,258 B1 | 1/2004 | Strom |
| 6,688,307 B2 | 2/2004 | Berthon-Jones |
| 6,694,978 B1 | 2/2004 | Bennarsten |
| 6,708,691 B1 | 3/2004 | Hayek |
| 6,718,974 B1 | 4/2004 | Moberg |
| 6,725,447 B1 | 4/2004 | Gilman et al. |
| 6,739,336 B1 * | 5/2004 | Jalde et al. ............... 128/204.21 |
| 6,739,337 B2 | 5/2004 | Isaza |
| 6,755,193 B2 | 6/2004 | Berthon-Jones et al. |
| 6,761,167 B1 | 7/2004 | Nadjafizadeh et al. |
| 6,761,168 B1 | 7/2004 | Nadjafizadeh et al. |
| 6,810,876 B2 | 11/2004 | Berthon-Jones |
| 6,814,074 B1 | 11/2004 | Nadjafizadeh et al. |
| 6,837,242 B2 | 1/2005 | Younes |
| 6,837,244 B2 | 1/2005 | Yagi et al. |
| 6,845,773 B2 | 1/2005 | Berthon-Jones et al. |
| 6,866,040 B1 | 3/2005 | Bourdon |
| 6,877,511 B2 | 4/2005 | DeVries et al. |
| 6,899,103 B1 | 5/2005 | Hood et al. |
| 6,920,875 B1 | 7/2005 | Hill et al. |
| 6,920,878 B2 | 7/2005 | Sinderby et al. |
| 6,929,006 B2 | 8/2005 | Kruger et al. |
| 6,932,084 B2 | 8/2005 | Estes et al. |
| 6,945,248 B2 | 9/2005 | Berthon-Jones |
| 6,948,497 B2 | 9/2005 | Zdrojkowski et al. |
| 6,956,572 B2 | 10/2005 | Zaleski |
| 6,960,854 B2 | 11/2005 | Nadjafizadeh et al. |
| 6,976,487 B1 | 12/2005 | Melker et al. |
| 6,988,994 B2 | 1/2006 | Rapoport et al. |
| 6,990,980 B2 | 1/2006 | Richey, II |
| 7,000,610 B2 | 2/2006 | Bennarsten et al. |
| 7,011,091 B2 | 3/2006 | Hill et al. |
| 7,013,892 B2 | 3/2006 | Estes et al. |
| 7,017,574 B2 | 3/2006 | Biondi et al. |
| 7,032,589 B2 | 4/2006 | Kerechanin, II et al. |
| 7,036,504 B2 | 5/2006 | Wallace et al. |
| 7,040,321 B2 | 5/2006 | Gobel |
| 7,077,131 B2 | 7/2006 | Hansen |
| RE39,225 E | 8/2006 | Isaza et al. |
| 7,086,098 B2 | 8/2006 | Sallvin |
| 7,096,866 B2 | 8/2006 | Be'eri et al. |
| 7,100,607 B2 | 9/2006 | Zdrojkowski et al. |
| 7,108,666 B2 | 9/2006 | Stenzler |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,195,594 B2 | 3/2007 | Eigler et al. |
| 7,219,666 B2 | 5/2007 | Friberg et al. |
| 7,225,013 B2 | 5/2007 | Geva et al. |
| 7,246,618 B2 | 7/2007 | Habashi |
| 7,255,103 B2 | 8/2007 | Bassin |
| 7,270,126 B2 | 9/2007 | Wallace et al. |
| 7,275,540 B2 | 10/2007 | Bolam et al. |
| 7,296,573 B2 | 11/2007 | Estes et al. |
| 7,305,987 B2 | 12/2007 | Scholler et al. |
| 7,334,578 B2 | 2/2008 | Biondi et al. |
| 7,343,917 B2 | 3/2008 | Jones |
| 7,347,205 B2 | 3/2008 | Levi |
| 7,367,338 B2 | 5/2008 | Baecke et al. |
| 7,369,757 B2 | 5/2008 | Farbarik |
| 7,370,650 B2 | 5/2008 | Nadjafizadeh et al. |
| RE40,402 E | 6/2008 | Leonhardt et al. |
| 7,428,902 B2 | 9/2008 | Du et al. |
| 7,460,959 B2 | 12/2008 | Jafari |
| 7,475,685 B2 | 1/2009 | Dietz et al. |
| 7,487,773 B2 | 2/2009 | Li |
| 7,530,353 B2 | 5/2009 | Choncholas et al. |
| 7,556,038 B2 | 7/2009 | Kirby et al. |
| 7,562,657 B2 | 7/2009 | Blanch et al. |
| 7,610,914 B2 | 11/2009 | Bolam et al. |
| 7,644,713 B2 | 1/2010 | Berthon-Jones |
| 7,654,802 B2 | 2/2010 | Crawford, Jr. et al. |
| 7,661,428 B2 | 2/2010 | Berthon-Jones |
| 7,694,677 B2 | 4/2010 | Tang |
| 7,717,113 B2 | 5/2010 | Andrieux |
| D618,356 S | 6/2010 | Ross |
| 7,740,591 B1 | 6/2010 | Starr et al. |
| 7,747,319 B2 | 6/2010 | Freeman |
| 7,783,353 B2 | 8/2010 | Libbus et al. |
| 7,784,461 B2 | 8/2010 | Figueiredo et al. |
| 7,802,571 B2 | 9/2010 | Tehrani |
| 7,810,496 B2 | 10/2010 | Estes et al. |
| 7,810,497 B2 | 10/2010 | Pittman et al. |
| 7,819,815 B2 | 10/2010 | Younes |
| 7,823,588 B2 | 11/2010 | Hansen |
| 7,849,854 B2 | 12/2010 | DeVries et al. |
| 7,855,716 B2 | 12/2010 | McCreary et al. |
| D632,796 S | 2/2011 | Ross et al. |
| D632,797 S | 2/2011 | Ross et al. |
| 7,886,739 B2 | 2/2011 | Soliman et al. |
| 7,891,354 B2 | 2/2011 | Farbarik |
| 7,893,560 B2 | 2/2011 | Carter |
| 7,918,223 B2 | 4/2011 | Soliman et al. |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |

(56) References Cited

U.S. PATENT DOCUMENTS

| | | |
|---|---|---|
| 8,302,602 B2 | 11/2012 | Andrieux et al. |
| 2001/0039950 A1 | 11/2001 | Scholler et al. |
| 2002/0023644 A1 | 2/2002 | Berthon-Jones |
| 2002/0148466 A1 | 10/2002 | Berthon-Jones |
| 2003/0000526 A1 | 1/2003 | Gobel |
| 2003/0079750 A1 | 5/2003 | Berthon-Jones |
| 2003/0111078 A1* | 6/2003 | Habashi .................. 128/204.18 |
| 2003/0127097 A1 | 7/2003 | Yurko |
| 2003/0225339 A1 | 12/2003 | Orr et al. |
| 2004/0173212 A1 | 9/2004 | Berthon-Jones |
| 2004/0206355 A1 | 10/2004 | Berthon-Jones et al. |
| 2004/0230105 A1 | 11/2004 | Geva et al. |
| 2004/0231670 A1 | 11/2004 | Bassin |
| 2005/0039748 A1 | 2/2005 | Andrieux |
| 2005/0109340 A1 | 5/2005 | Tehrani |
| 2005/0121033 A1 | 6/2005 | Starr et al. |
| 2005/0139212 A1* | 6/2005 | Bourdon .................. 128/204.23 |
| 2005/0211246 A1 | 9/2005 | Beck et al. |
| 2005/0211248 A1 | 9/2005 | Lauk et al. |
| 2005/0279358 A1 | 12/2005 | Richey, II |
| 2006/0011195 A1 | 1/2006 | Zarychta |
| 2006/0069326 A1 | 3/2006 | Heath |
| 2006/0070624 A1* | 4/2006 | Kane et al. ............... 128/204.23 |
| 2006/0086357 A1 | 4/2006 | Soliman et al. |
| 2006/0118112 A1 | 6/2006 | Cattano et al. |
| 2006/0150974 A1 | 7/2006 | Berthon-Jones |
| 2006/0155206 A1 | 7/2006 | Lynn |
| 2006/0155207 A1 | 7/2006 | Lynn et al. |
| 2006/0155336 A1 | 7/2006 | Heath |
| 2006/0162727 A1 | 7/2006 | Biondi et al. |
| 2006/0174884 A1 | 8/2006 | Habashi |
| 2006/0235324 A1 | 10/2006 | Lynn |
| 2006/0249148 A1 | 11/2006 | Younes |
| 2006/0278223 A1 | 12/2006 | Younes |
| 2006/0283451 A1 | 12/2006 | Albertelli |
| 2007/0017515 A1 | 1/2007 | Wallace et al. |
| 2007/0044796 A1 | 3/2007 | Zdrojkowski et al. |
| 2007/0044799 A1 | 3/2007 | Hete et al. |
| 2007/0077200 A1 | 4/2007 | Baker |
| 2007/0089745 A1 | 4/2007 | Gabriel et al. |
| 2007/0101992 A1 | 5/2007 | Soliman et al. |
| 2007/0157930 A1 | 7/2007 | Soliman et al. |
| 2007/0162097 A9 | 7/2007 | Rojas |
| 2007/0163584 A1 | 7/2007 | Bohm et al. |
| 2007/0215146 A1 | 9/2007 | Douglas et al. |
| 2007/0221224 A1 | 9/2007 | Pittman et al. |
| 2007/0227537 A1 | 10/2007 | Bemister et al. |
| 2007/0251527 A1 | 11/2007 | Sleeper |
| 2007/0283958 A1 | 12/2007 | Naghavi |
| 2007/0284361 A1 | 12/2007 | Nadjafizadeh et al. |
| 2008/0000475 A1 | 1/2008 | Hill |
| 2008/0011301 A1 | 1/2008 | Qian |
| 2008/0035147 A1 | 2/2008 | Kirby et al. |
| 2008/0045813 A1 | 2/2008 | Phuah et al. |
| 2008/0045845 A1 | 2/2008 | Pfeiffer et al. |
| 2008/0053441 A1 | 3/2008 | Gottlib et al. |
| 2008/0053443 A1 | 3/2008 | Estes et al. |
| 2008/0053444 A1 | 3/2008 | Estes et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0236582 A1* | 10/2008 | Tehrani .................. 128/204.22 |
| 2008/0243007 A1 | 10/2008 | Liao et al. |
| 2008/0257349 A1 | 10/2008 | Hedner et al. |
| 2008/0295839 A1 | 12/2008 | Habashi |
| 2008/0295840 A1 | 12/2008 | Glaw |
| 2009/0020120 A1 | 1/2009 | Schatzl et al. |
| 2009/0020121 A1 | 1/2009 | Bassin |
| 2009/0024008 A1 | 1/2009 | Brunner et al. |
| 2009/0038616 A1 | 2/2009 | Mulcahy et al. |
| 2009/0050154 A1 | 2/2009 | Strothmann et al. |
| 2009/0078255 A1 | 3/2009 | Bowman et al. |
| 2009/0078258 A1 | 3/2009 | Bowman et al. |
| 2009/0084381 A1 | 4/2009 | DeVries et al. |
| 2009/0114224 A1 | 5/2009 | Handzsuj et al. |
| 2009/0120439 A1 | 5/2009 | Goebel |
| 2009/0151719 A1 | 6/2009 | Wondka et al. |
| 2009/0151724 A1 | 6/2009 | Wondka et al. |
| 2009/0165795 A1 | 7/2009 | Nadjafizadeh et al. |
| 2009/0171176 A1 | 7/2009 | Andersohn |
| 2009/0205661 A1 | 8/2009 | Stephenson et al. |
| 2009/0205663 A1* | 8/2009 | Vandine et al. .......... 128/204.23 |
| 2009/0241952 A1 | 10/2009 | Nicolazzi et al. |
| 2009/0241953 A1 | 10/2009 | Vandine et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0277447 A1 | 11/2009 | Voss et al. |
| 2009/0293877 A1 | 12/2009 | Blanch et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0095961 A1 | 4/2010 | Thronesel et al. |
| 2010/0095964 A1 | 4/2010 | Tham et al. |
| 2010/0100000 A1 | 4/2010 | Lee et al. |
| 2010/0101576 A1 | 4/2010 | Berthon-Jones |
| 2010/0106037 A1 | 4/2010 | Kacmarek et al. |
| 2010/0106208 A1 | 4/2010 | Freeman |
| 2010/0125227 A1 | 5/2010 | Bird |
| 2010/0139660 A1 | 6/2010 | Adahan |
| 2010/0147303 A1 | 6/2010 | Jafari et al. |
| 2010/0186744 A1 | 7/2010 | Andrieux |
| 2010/0204622 A1 | 8/2010 | Hwang et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0236555 A1 | 9/2010 | Jafari et al. |
| 2010/0242961 A1 | 9/2010 | Mougel et al. |
| 2010/0249559 A1 | 9/2010 | Lovejoy |
| 2010/0262116 A1 | 10/2010 | Sowb |
| 2010/0275920 A1 | 11/2010 | Tham et al. |
| 2010/0282259 A1 | 11/2010 | Figueiredo et al. |
| 2010/0286740 A1 | 11/2010 | Libbus et al. |
| 2010/0288279 A1 | 11/2010 | Seiver et al. |
| 2010/0288283 A1 | 11/2010 | Campbell et al. |
| 2010/0300445 A1 | 12/2010 | Chatburn et al. |
| 2010/0300446 A1 | 12/2010 | Nicolazzi et al. |
| 2010/0324437 A1 | 12/2010 | Freeman et al. |
| 2011/0011160 A1 | 1/2011 | Gerde |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |

(56) References Cited

U.S. PATENT DOCUMENTS

| | | |
|---|---|---|
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272961 A1 | 11/2012 | Masic et al. |
| 2012/0272962 A1 | 11/2012 | Doyle et al. |

FOREIGN PATENT DOCUMENTS

| | | |
|---|---|---|
| WO | WO9014852 | 12/1990 |
| WO | WO9806449 | 2/1998 |
| WO | WO9812965 | 4/1998 |
| WO | WO0010634 | 3/2000 |
| WO | WO2004096333 | 11/2004 |
| WO | WO2006012205 | 2/2006 |
| WO | WO2007047172 | 4/2007 |
| WO | WO2009123977 | 10/2009 |
| WO | WO2010036655 | 4/2010 |
| WO | WO2010036816 | 4/2010 |
| WO | WO2010111073 | 9/2010 |

OTHER PUBLICATIONS

7200 Ventilatory System: Addendum/Errata. Nellcor Puritan Bennett, Part No. 4-023576-00, Rev. A, Apr. 1988.

800 Operator's and Technical Reference Manual. Series Ventilator System, Nellcor Puritan Bennett, Part No. 4-070088-00, Rev. L, Aug. 2010.

840 Operator's and Technical Reference Manual. Ventilator System, Nellcor Puritan Bennett, Part No. 4-075609-00, Rev. G, Oct. 2006.

BiLevel option/800 Series Ventilators, 4-075816-00 Rev. A, (10/98), Jul. 25, 2000, pp. 1-8.

Burchardi, H. "New Strategies in Mechanical Ventilation for Acute Lung Injury," Series Clinical Physiology in Respiratory Intesive Cate, European Respiratory Journal, 1996, pp. 1063-1072.

Companion 320 I/E Bi-Level Respiratory System. Service Manual Part No. 6-799950-00, Puritan Bennett, Service Manual Rev A. May 1993, pp. 1-60.

Companion 320 Service Procedure. Puritan Bennett, Lenexa Medical Division, Service Department, SD-005, B01, 6968A, 1993, pp. 1-20.

Companion 320. Puritan Bennett, Lenexa Medical Division, Product Specification, PS1012, B02, 7267A, 1993, pp. 1-21.

Downs, J. et al. "Airway Pressure Release Ventilation: A New Concept in Ventilatory Support," Critical Care Medicine, May 1987, vol. 15, No. 5, pp. 459-461.

Frawley, P. Milo et al. "Airway Pressure Release Ventilation: Theory and Practice," AACN Clinical Issues: Advanced Practice in Acute and Critical Care, vol. 12, No. 2, May 2001, pp. 234-246.

Maria I. Rudis, PharmD, BCPS et al., Economic Impact of Prolonged Motor Weakness Complicating Neuromuscular Blockade in the Intensive Care Unit, 24(10) Critical Care Med. 1749, 1749-1756 (1996).

Martin, Lynn D. et al. "Optimal Release Time During Airway Pressure Release Ventilation in Neonatal Sheep," Critical Care Medicine, Mar. 1994, vol. No. 3, pp. 486-493.

Roy G. Brower, M.D. et al., Ventilation with Lower Tidal Volumes as Compared with Traditional Tidal Volumes for Acute Lung Injury and the Acute Respiratory Distress Syndrome, 342(18) New Eng. J. Med. 1301, 1301-08 (2000).

Stock, M. Christine, et al. "Airway Pressure Release Ventilation," Critical Care Medicine, vol. 15, No. 5, May 1987, pp. 462-466.

Sydow, M., et al. "Long-term Effects of Two Different Ventilatory Modes on Oxygenation in Acute Lung Injury: Comparison of Airway Pressure Release Ventilation and Volume-controlled Inverse Ratio Ventilation," American Journal of Repiratory and Critical Care Medicine, vol. 149, 1994, pp. 1550-1556.

Valentine, Dwight et al. "Distribution of Ventilation and Perfusion with Different Modes of Mechanical Ventilation1-3," V A/Q Distribution with Different Ventilaotry Modes, Am Rev Respir Dis, Jan. 1991, pp. 1262-1266.

Volume Ventilation Plus option Addendum. 800 Series, 4-070178-00 Rev. B, Oct. 2002, pp. 1-16.

* cited by examiner

METHODS AND SYSTEMS FOR VOLUME-TARGETED MINIMUM PRESSURE-CONTROL VENTILATION

INTRODUCTION

Medical ventilator systems have long been used to provide ventilatory and supplemental oxygen support to patients. These ventilators typically comprise a source of pressurized oxygen which is fluidly connected to the patient through a conduit or tubing. As each patient may require a different ventilation strategy, modern ventilators can be customized for the particular needs of an individual patient. For example, several different ventilator modes have been created to provide better ventilation for patients in various different scenarios.

Volume-Targeted Minimum Pressure-Control Ventilation

This disclosure describes systems and methods for providing a volume-targeted minimum pressure-control breath type during ventilation of a patient. The disclosure describes a novel breath type that allows an operator to input a tidal volume and receive some of the benefits of utilizing an airway pressure release ventilation (APRV) breath type in combination with some of the benefits of utilizing a volume-targeted-pressure-control (VC+) breath type.

In part, this disclosure describes a method for ventilating a patient with a ventilator. The method includes:

a) receiving a tidal volume and a PEEP;
b) receiving a minimum inspiration pressure;
c) receiving at least two of an inspiration time, an exhalation time, an I:E ratio, and a respiratory rate;
d) calculating a calculated pressure based on measurements taken from a previous inspiration indicative of tidal volume delivered to the patient;
e) comparing the calculated pressure to the received minimum inspiration pressure;
delivering a delivered inspiration pressure during a next inhalation to the patient, the delivered inspiration pressure determined based on the step of comparing the calculated pressure to the received minimum inspiration pressure; and
f) delivering, after the next inhalation, the received PEEP.

Yet another aspect of this disclosure describes a ventilator system that includes: a pressure generating system adapted to generate a flow of breathing gas; a ventilation tubing system including a patient interface for connecting the pressure generating system to a patient; one or more sensors operatively coupled to at least one of the pressure generating system, the patient, and the ventilation tubing system, wherein at least one sensor is capable of generating an output indicative of an inspiration flow; and a VCI module that calculates an inspiration pressure based on a received tidal volume from the output indicative of the inspiration flow and causes the pressure generating system to deliver at least one of a calculated pressure or a received minimum pressure to the patient during inhalation.

The disclosure further describes a computer-readable medium having computer-executable instructions for performing a method for ventilating a patient with a ventilator. The method includes:

a) repeatedly receiving a tidal volume and a PEEP;
b) repeatedly receiving a minimum inspiration pressure;
c) repeatedly receiving at least two of an inspiration time, an exhalation time, an I:E ratio, and a respiratory rate;
d) repeatedly calculating a calculated pressure based on measurements taken from a previous inspiration indicative of tidal volume delivered to the patient;
e) repeatedly comparing the calculated pressure to the received minimum inspiration pressure;
f) repeatedly delivering a delivered inspiration pressure during a next inhalation to the patient, the delivered inspiration pressure determined based on the step of comparing the calculated pressure to the received minimum inspiration pressure; and
g) repeatedly delivering, after the next inhalation, the received PEEP.

The disclosure also describes a ventilator system including means for means for receiving a tidal volume and a PEEP; means for receiving a minimum inspiration pressure; means for receiving at least two of an inspiration time, an exhalation time, an I:E ratio, and a respiratory rate; means for calculating a calculated pressure based on measurements taken from a previous inspiration indicative of tidal volume delivered to the patient; means for comparing the calculated pressure to the received minimum inspiration pressure; means for delivering a delivered inspiration pressure during a next inhalation to the patient, the delivered inspiration pressure determined based on the step of comparing the calculated pressure to the received minimum inspiration pressure; and means for delivering, after the next inhalation, the received PEEP.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The following drawing figures, which form a part of this application, are illustrative of embodiments of systems and methods described below and are not meant to limit the scope of the invention in any manner, which scope shall be based on the claims appended hereto.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described in the context of a medical ventilator for human patients could be adapted for use with other systems such as ventilators for non-human patients and general gas transport systems.

Medical ventilators are used to provide a breathing gas to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gas having a desired concentration of oxygen is supplied to the patient at desired pressures and rates. Ventilators capable of operating independently of external sources of pressurized air are also available.

While operating a ventilator, it is desirable to control the percentage of oxygen in the gas supplied by the ventilator to the patient. Further, as each patient may require a different ventilation strategy, modern ventilators can be customized for the particular needs of an individual patient. For example, several different ventilator breath types have been created to provide better ventilation for patients in various different scenarios.

Volume ventilation refers to various forms of volume-targeted ventilation that utilize a clinician set tidal volume to regulate some aspect of the delivery of gas (e.g., inhalation pressure, inhalation duration, cycling criteria, etc.) to the patient. Different types of volume ventilation are available depending on the specific implementation of volume regulation. For example, for volume-cycled ventilation, an end of inspiration is determined based on monitoring the volume delivered to the patient. Volume ventilation may include volume-control (VC) breath type. Another form of volume ventilation is that in which the pressure delivered during inhalation is some function of a clinician-set tidal volume target. Volume-targeted-pressure-control (VC+), or volume-support (VS) breath types are examples of this type of volume ventilation.

A landmark study published by The New England Journal of Medicine was conducted in the year 2000 that utilized volume-control ventilation on airway respiratory distress syndrome (ARDS) patients.[1] ARDS is caused by a variety of different direct and indirect issues, which impairs gas exchange in the lungs. This study found a significant reduction in mortality when 4-6 ml/kg of tidal volume in VC ventilation was utilized on ARDS patients. This study is the most widely accepted study in the United States and still drives the use of VC ventilation today. Accordingly, most clinicians are familiar with VC ventilation and its settings. However, VC ventilation is a mandatory mode that is often found to be very uncomfortable by patients. Many patients fight the mandatory settings of this mode requiring them to be sedated. Sedation of patients has been shown to increase costs by $66,000.[2]

[1] Roy G. Brower, M. D. et al., Ventilation with Lower Tidal Volumes as Compared with Traditional Tidal Volumes for Acute Lung Injury and the Acute Respiratory Distress Syndrome, 342(18) NEW ENG. J. MED. 1301, 1301-08 (2000).
[2] Maria I. Rudis, PharmD, BCPS et al., Economic Impact of Prolonged Motor Weakness Complicating Neuromuscular Blockade in the Intensive Care Unit, 24(10) CRITICAL CARE MED. 1749, 1749-1756 (1996).

Pressure-targeted breath types may be provided by regulating the pressure delivered to the patient in various ways. For example, during pressure-cycled ventilation, an end of inspiration is determined based on monitoring the pressure delivered to the patient. Pressure ventilation may include a pressure-support (PS), a proportional assist (PA), or a pressure-control (PC) breath type, for example. Pressure ventilation may also include various forms of BiLevel™ (BL) ventilation, i.e., pressure ventilation in which the inhalation positive airway pressure (IPAP) is higher than the exhalation positive airway pressure (EPAP).

The different breath types may also be provided as part of a BiLevel™ (BL) mode of ventilation. In BL mode the ventilator delivers breaths (either spontaneous or controlled breaths) while cycling between two exhalation pressure levels over time so that all breaths being delivered during a first period will use a first low exhalation pressure ($PEEP_L$) and all breaths delivered during the second period will use a second, higher, exhalation pressure ($PEEP_H$). The transition between $PEEP_L$ and $PEEP_H$ may be synchronized to a patient's spontaneous breathing efforts and/or to the ventilator-controlled breaths.

BL mode ventilation is one approach being utilized today to treat ARDS patients in an attempt to decrease sedation. In order to treat ARDS patients, the BLmode is set with an inspiration to expiration (I:E) ratio inverse enough to become similar to airway pressure release ventilation (APRV) (e.g., I:E ratio of 5:1). This current strategy is also being promoted by the American Association for Respiratory Care as a ventilation strategy for H1N1 patients.

Clinicians are increasing the use of BL mode ventilation. However, BL mode requires setting a $PEEP_H$ and $PEEP_L$, which are very different from the tidal volume setting of the more commonly utilized volume control breath types. Accordingly, several clinicians are hesitant to utilize BL mode ventilation, since they would have to learn an entirely new system for setting, managing, and watching this type of ventilation. Further, as lung compliance changes in patients being ventilated in BL mode, volume can exceed desired levels.

As discussed above, the VC+ breath type is a combination of volume and pressure control breath types that may be delivered to a patient as a mandatory breath. In particular, VC+ may provide the benefits associated with setting a target tidal volume, while also allowing for variable flow. Variable flow may be helpful in meeting inhalation flow demands for actively breathing patients. In the VC+ breath type, the inspiration pressure (P) for a breath is calculated based on the measured tidal volume of the prior breath. When a patient spontaneously pulls under the patient's own effort a large amount of tidal volume in a breath, the VC+ breath type provides for less $P_I$ in the next or following breath in an attempt to achieve the set tidal volume. Accordingly, based on the previous breath, the patient could receive little or no assistance in the form of inspiration pressure support during the VC+ breath type in this situation.

Unlike VC in which tidal volume of each breath is essentially guaranteed, when the set inhalation time is reached the ventilator initiates exhalation in a VC+ breath type regardless of actual tidal volume delivered in that breath. Exhalation lasts from the end of inspiration until the beginning of the next inspiration. For a non-triggering patient, the exhalation time ($T_E$) is based on the respiratory rate set by the clinician. Upon the end of exhalation, another VC+ mandatory breath is given to the patient. By controlling target tidal volume and allowing for variable flow, VC+ allows a clinician to maintain the volume while allowing the flow and pressure targets to fluctuate from breath to breath. Providing the patient with the ability to fluctuate flow as desired is often found by patients to be more comfortable than mandatory volume control modes.

However, the VC+ breath type is not an ideal mode for ARDS patients because pressure lowers in VC+ as the patient increases their spontaneous efforts to pull more tidal volume on their own and could result in insufficient inspiration pressure support. ARDS patients require a minimum level of pressure support to promote gas exchange within their lungs. Further, the VC+ breath type does not allow for an I:E ratio of greater than 4:1, which is beneficial to ARDS patients.

The current disclosure describes a volume targeted airway pressure release ventilation with guaranteed minimal pressure or a volume-targeted minimum pressure-control (VCI) breath type that combines the benefits of VC+ with the benefits of BL and reduces the disadvantages of each for the ventilation of patients, such as the ventilation of weak patients with ARDS and H1N1. The VCI breath type allows the clinician to set a tidal volume, which more clinicians are familiar with, while still receiving the benefits of pressure ventilation. The VCI breath type is similar to the VC+ breath type, except, the VCI breath type provides a minimum inspiration pressure ($P_{MIN}$) and allows for an inverse I:E ratio of greater than 4:1. This inverse I:E ratio is represented in the letter "I" of the VCI abbreviation. Further, the VCI breath type is different from the VC+ breath type because the VCI breath type allows the patient to spontaneously trigger inspirations above the given $P_i$ during the inhalation period and PEEP during the exhalation period and tracks these spontaneously triggered inspirations. The VCI breath type may additionally provide pressure support for detected spontaneously triggered inspirations above the given $P_i$ and PEEP.

Figure 1:
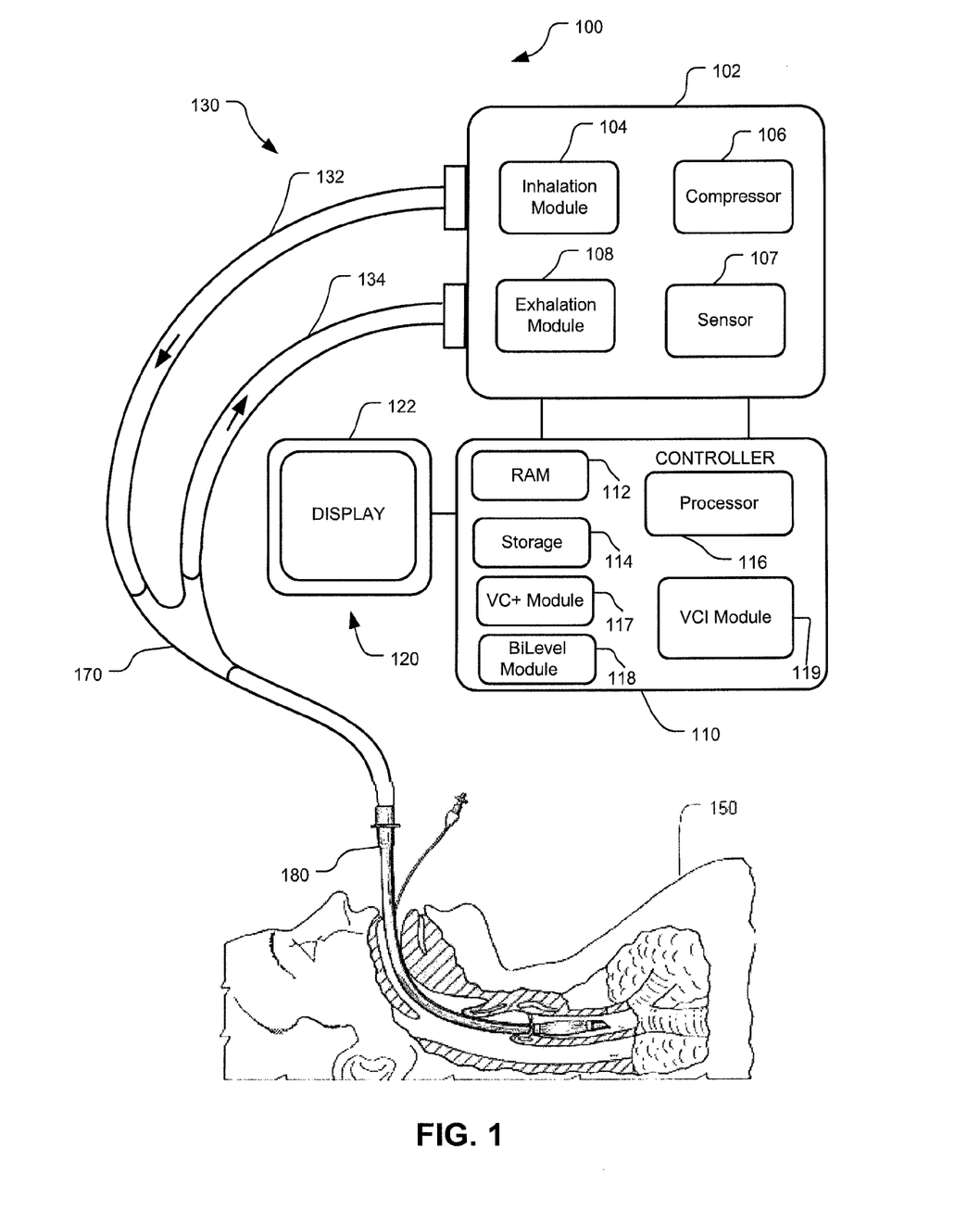
FIG. 1 illustrates an embodiment of a ventilator.

FIG. 1 is a diagram illustrating an embodiment of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inhalation limb 132 and an exhalation limb 134 of the ventilation tubing system 130.

Pneumatic system 102 may be configured in a variety of ways. In the present example, pneumatic system 102 includes an exhalation module 108 coupled with the exhalation limb 134 and an inhalation module 104 coupled with the inhalation limb 132. Compressor 106 or other source(s) of pressurized gases (e.g., air, oxygen, and/or helium) is coupled with inhalation module 104 and the exhalation module 108 to provide a gas source for ventilatory support via inhalation limb 132.

The inhalation module 104 is configured to deliver gases to the patient 150 according to prescribed ventilatory settings. In some embodiments, inhalation module 104 is configured to provide ventilation according to various breath types, e.g., via VC, PC, VC+, or VCI or via any other suitable breath types.

The exhalation module 108 is configured to release gases from the patient's lungs according to prescribed ventilatory settings. Specifically, exhalation module 108 is associated with and/or controls an exhalation valve for releasing gases from the patient 150. In some embodiments, exhalation module 108 is configured to provide exhalation according to various breath types, e.g., via VC, PC, VC+, or VCI or via any other suitable breath types.

The ventilator 100 may also include one or more sensors 107 communicatively coupled to ventilator 100. The sensors 107 may be located in the pneumatic system 102, ventilation tubing system 130, and/or on the patient 150. The embodiment of FIG. 1, illustrates a sensor 107 in pneumatic system 102.

Sensors 107 may communicate with various components of ventilator 100, e.g., pneumatic system 102, other sensors 107, processor 116, volume-targeted minimal pressure-control (VCI) module 119, and any other suitable components and/or modules. In one embodiment, sensors 107 generate output and send this output to pneumatic system 102, other sensors 107, processor 116, VCI module 119, and any other suitable components and/or modules. Sensors 107 may employ any suitable sensory or derivative technique for monitoring one or more parameters associated with the ventilation of a patient 150. Sensors 107 may detect changes in ventilatory parameters indicative of patient triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inhalation and/or exhalation modules for detecting changes in, for example, circuit pressure and/or flow. In other examples, sensors 107 may be affixed to the ventilatory tubing or may be embedded in the tubing itself. According to some embodiments, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with embodiments described herein.

The pneumatic system 102 may include a variety of other components, including mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment the operator interface 120 of the ventilator 100 includes a display 122 communicatively coupled to ventilator 100. Display 122 provides various input screens, for receiving clinician input, and various display screens, for presenting useful information to the clinician. In one embodiment, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient. The useful information may be derived by the ventilator 100, based on data collected by a processor 116, and the useful information may be displayed to the clinician in the form of graphs, wave representations, pie graphs, or other suitable forms of graphic display. For example, patient data may be displayed on the GUI and/or display 122. Additionally or alternatively, patient data may be communicated to a remote monitoring system coupled via any suitable means to the ventilator 100.

Controller 110 may include memory 112, one or more processors 116, storage 114, and/or other components of the type commonly found in command and control computing devices. Controller 110 may further include a volume-targeted pressure-controlled (VC+) module 117, a BiLevel™ (BL) module 118, and/or a volume-targeted minimum pressure-controlled (VCI) module 119 configured to deliver gases to the patient 150 according to a prescribed breath type as illustrated in FIG. 1. In alternative embodiments, VC+ module 117, the BL module 118, and VCI module 119 configured to deliver gases to the patient 150 according to a prescribed breath type may be located in other components of the ventilator 100, such as in the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

In some embodiments, the inhalation module 104 and/or the exhalation module 108 receive commands or instructions for executing a breath type from a VC+ module 117, a BL module 118, or a VCI module 119. In some embodiments, the controller 110 receives commands or instructions for executing a breath type from the VC+ module 117, the BL module 118, or the VCI module 119. In other embodiments, the pneumatic system 102 receives commands or instructions for executing a breath type from the VC+ module 117, the BL module 118, or the VCI module 119. In further embodiments, not shown, the VC+ module 117, the BL module 118, or the VCI module 119 are located separate from the controller 110, within the pneumatic system 102, or separate from the controller 110 and the pneumatic system 102.

The VC+ module 117 provides instructions or commands for executing a volume-targeted pressure-controlled breath type as described above. The BL module 118 provides instructions or commands for operating the ventilator in the BiLevel™ mode while delivering any of the various breath type as described above. The VCI module 119 provides instructions or commands for executing a volume-targeted airway pressure release ventilation with a guaranteed minimal pressure or a volume-targeted minimum pressure-controlled breath type. The purpose of the VCI breath type is to utilize the benefits of VC+ and BL while reducing the disadvantages of these breath types during the ventilation of patients, such as weak patients with H1N1 and ARDS patients.

The VCI module 119 provides instructions for the delivery of a VCI breath type based on a received tidal volume. One of the major hurdles to the use of BL is clinician unfamiliarity. Because clinicians are unfamiliar with setting $PEEP_H$ and $PEEP_L$, many choose to use familiar volume control breath types instead of learning a new, different breath type. Most clinicians are familiar with setting a tidal volume making the use of a VCI breath type an easier transition. Further, the received limitation on tidal volume helps to prevent patients from receiving more than a desired tidal volume of gas. The VCI module 119 provides similar instruction to the inhalation and exhalation module as the VC+ module 117 except the VCI module 119 provides instructions for a minimum inspiration pressure ($P_{MIN}$) and allows a VCI breath type with an inverse I:E ratio of greater than 4:1.

The VCI module 119 provides instructions that require the VCI breath type to maintain a $P_{MIN}$, unlike the VC+ module 117 that allows $P_i$ to fall to zero. The VCI module 119 compares the calculated $P_i$ to the $P_{MIN}$. If the calculated $P_i$ is less than the $P_{MIN}$, the VCI module 119 provides instructions to deliver the $P_{MIN}$ in the next or following inspiration. If the calculated $P_i$ is at least the $P_{MIN}$, then the VCI module 119 provides instructions to deliver the calculated $P_i$ in the next or following inspiration. In some embodiments, the $P_{MIN}$ is input or selected by the operator. In other embodiments, the $P_{MIN}$ is determined by the ventilator based on or derived from other ventilator parameters, patient parameters, and/or operator input. In some embodiments, the ventilator utilizes a stored default value for $P_{MIN}$ if the operator does not select or input a $P_{MIN}$.

In some embodiments, the VCI module 119 provides instructions that require the VCI breath type to maintain a pressure maximum ($P_{MAX}$), unlike the VC+ module 117 that allows $P_i$ to rise to any calculated level based on the amount of tidal volume pulled in the previous breath. The VCI module 119 compares the calculated $P_i$ to the $P_{MAX}$. If the calculated $P_i$ is more than the $P_{MAX}$, the VCI module 119 provides instructions to deliver the $P_{MAX}$ in the next or following inspiration. If the calculated $P_i$ is at least the $P_{MAX}$, then the VCI module 119 provides instructions to deliver the calculated $P_i$ in the next or following inspiration. In some embodiments, the $P_{MAX}$ is input or selected by the operator. In other embodiments, the $P_{MAX}$ is determined by the ventilator based on or derived from other ventilator parameters, patient parameters, and/or operator input, such as $P_{MIN}$. In some embodiments, the ventilator utilizes a stored default value for $P_{MAX}$ if the operator does not select or input a $P_{MAX}$.

The VCI module 119 determines the respiration rate and I:E ratio by receiving at least two of an inspiration time, an exhalation time, an I:E ratio, and a respiratory rate. Depending upon the received parameters, the VCI module 119 will send instructions for an inverse I:E ratio of greater than 4:1 as would be allowed by the BL module 118 and unlike the VC+ module 117 that will only provide instructions for an I:E ratio of 4:1 or less. This inverse ratio is particularly beneficial to ARDS patients and other weak patients, such as H1N1 patients.

In some embodiments, the VCI module 119 further receives a fractional inspired oxygen setting ($FiO_2$) for controlling the VCI breath type. In some embodiments, the VCI module 119 further receives a PEEP for controlling the VCI breath type. In other embodiments, the VCI module 119 further receives a rise time for controlling the VCI breath type. As discussed above, the, VCI module 119 may further receive a $P_{MIN}$ and/or a $P_{MAX}$ for controlling the VCI breath type.

Further, the VCI module 119 detects patient initiated triggers above the given $P_i$ and PEEP during inspiration and exhalation based on received sensor data and information similar to the BL module 118, which allows and tracks patient triggered spontaneous inspirations above the given $PEEP_H$ and $PEEP_L$. The VCI module 119 sends instructions allowing the patient to pull additional volume above what is provided at $P_i$ and PEEP based on detected patient initiated triggers. While the VCI module 119 tracks each patient initiated trigger, including, number, duration, volume, pressure, etc., the VCI module 119 does not utilize this information in the calculation of the next $P_i$. VCI module 119 calculates the $P_i$ for the next inhalation based solely on the amount of tidal volume taken by the patient during the delivery of the previous $P_i$ for the initiation of inhalation. In one embodiment, the tidal volume is calculated based on an output indicative of an inspiration flow from a sensor 107.

Additionally, the VCI module 119 may provide instructions for providing pressure support to any detected patient initiated breath above the delivered PEEP and $P_i$ based on a received pressure support ($P_{SUPP}$) setting, which is similar to the BL module 118 that provides instructions for supporting detected patient initiated inspirations above the set $PEEP_H$ and $PEEP_L$ based on a received $P_{SUPP}$ setting. The $P_{SUPP}$ setting may be any parameter for providing additional pressure as known by a person of skill in the art for ventilating a patient. For example, the $P_{SUPP}$ may vary based on the amount of volume pulled by the patient or may be a set amount or percent of pressure that is given regardless of the amount of volume pulled by the patient.

Any suitable type of triggering detection for determining a patient trigger may be utilized by the ventilation system, such as nasal detection, diaphragm detection, and/or brain signal detection. Further, patient triggering may be detected via a pressure-monitoring method, a flow-monitoring method, direct or indirect measurement of neuromuscular signals, or any other suitable method. Sensors suitable for this detection may include any suitable sensing device as known by a person of skill in the art for a ventilator.

As used herein, any parameters received by the VCI module 119 are input by the clinician, selected by the clinician, or provided by the ventilator. The ventilator may derive the received parameter based on patient parameters, ventilator parameters, and/or input or selected clinician data. In some embodiments, the ventilator contains stored default values, which the ventilator utilizes as the received parameter when the clinician does not input or select a parameter.

Figure 2:
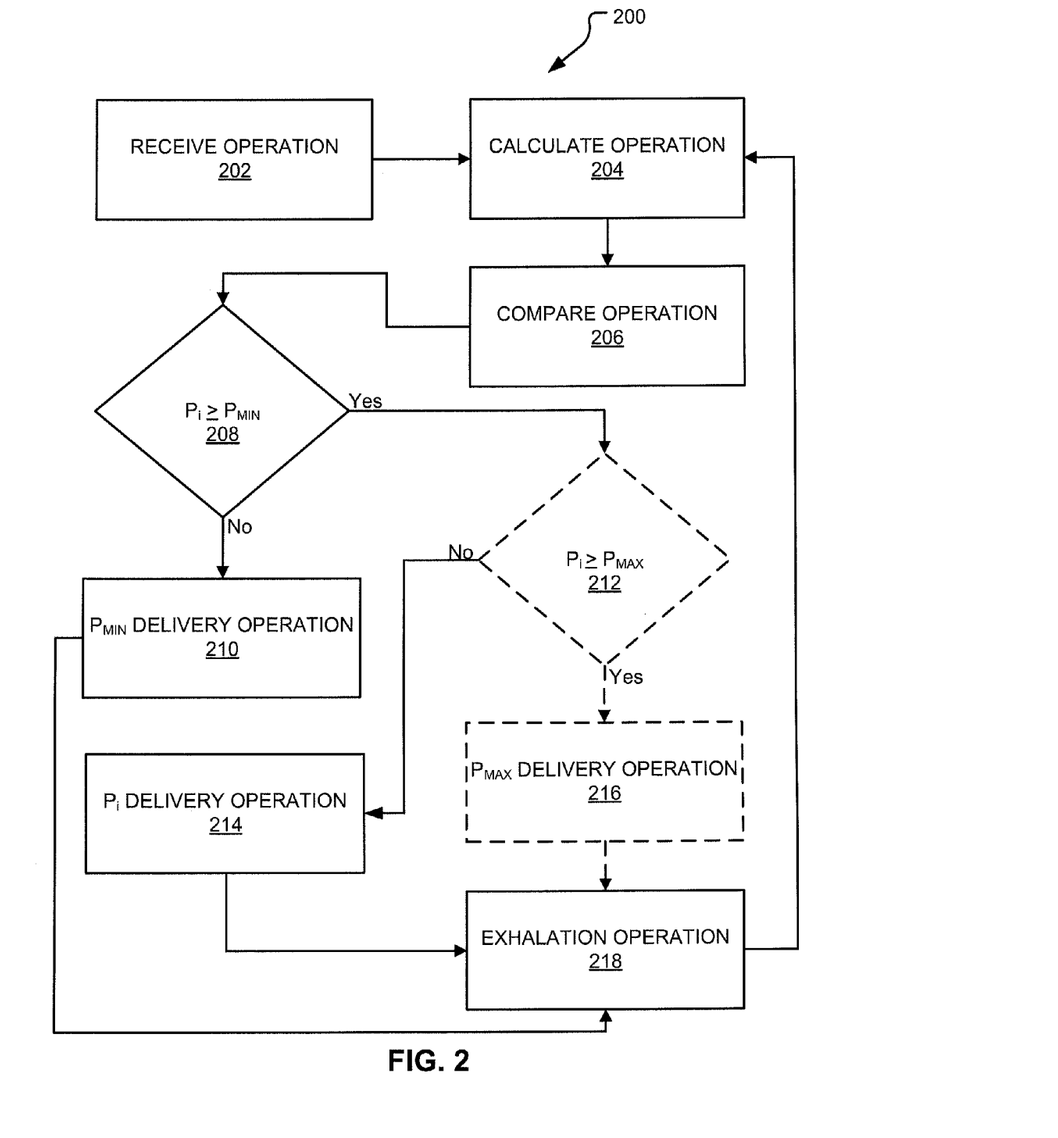
FIG. 2 illustrates an embodiment of a method for ventilating a patient on a ventilator with a VCI breath type.

FIG. 2 illustrates an embodiment of a method 200 for ventilating a patient on a ventilator with a VCI breath type. As illustrated, method 200 includes a receive operation 202. During the receive operation 202, the ventilator determines or receives a tidal volume, a PEEP, a $P_{MIN}$, and at least two of a respiration rate, an inhalation time, an expiration time, or an I:E ratio, such as via direct selections of a value for each parameter made by a clinician. The received parameters may be saved default settings stored within the ventilator, input by a clinician, chosen by a clinician, and/or derived by the ventilator based on other patient parameters, ventilator parameters, or inputted parameters. In some embodiments, during the receive operation 202, the ventilator further determines or receives $FiO_2$, rise time, $P_{SUPP}$, and/or $P_{MAX}$.

In some embodiments, the operator inputs or selects the received tidal volume and/or PEEP for the VCI breath type during receive operation 202. One of the major hurdles to the use of BL is clinician unfamiliarity. Because clinicians are unfamiliar with setting $PEEP_H$ and $PEEP_L$, many chose to use familiar volume control breath types instead of learning a new, different breath type. Most clinicians are familiar with setting a tidal volume making the use of a VCI breath type an easier transition. Further, the received tidal volume helps to prevent patients from receiving more than a desired tidal volume of gas.

In some embodiments, when the operator does not input a tidal volume and/or $PEEP_i$ the ventilator receives the tidal volume and/or PEEP from a stored default value during receive operation 202. In further embodiments, the ventilator derives the stored default values based on other ventilator or patient parameters. The ventilator performs the receive operation 202 anytime the ventilator receives a new tidal volume, a new PEEP, a new $P_{MIN}$, and at least two of a new respiration rate, a new inhalation time, a new expiration time, or a new I:E ratio, such as via direct selections by a clinician.

Further, the ventilator during receive operation 202 determines the respiration rate and the I:E ratio by receiving at least two of an inspiration time, an exhalation time, an I:E ratio, and a respiratory rate. Unlike a VC+ breath type, the ventilator in the receive operation 202 will accept parameters that lead to an inverse I:E ratio of greater than 4:1. VC+ breath types only allow for an I:E ratio of 4:1 or less. The inverse I:E ratio of greater than 4:1 is, however, often utilized during BL breath types. This inverse ratio is particularly beneficial for ARDS patients and other weak patients, such as H1N1 patients.

As discussed above, the VCI breath type utilizes measurements from the previous breath to determine an inspiration pressure to delivery in a next breath. Accordingly, if no data has been collected by the ventilator, the ventilator during method 200 cannot calculate an inspiration pressure for delivery in the next breath. In one embodiment, this is addressed by calculating or selecting a default inspiration pressure to be used for the initial breath. The ventilator during method 200 delivers a test breath at the beginning of the VCI breath type when no data has been collected. The test breath is a VC breath that delivers the initial pressure. In some embodiments, the default pressure is derived from the received tidal volume. Alternatively, the default pressure may be determined from the patient's ideal body weight, previous treatment pressures, or any other factor.

Further, method 200 includes a calculate operation 204. The calculate operation 204 is performed by the ventilator at the beginning of each breath. During the calculate operation 204, the ventilator calculates an inspiration pressure based on measurements taken from the previously delivered inspiration including the test breath. In an embodiment, the ventilator during calculate operation 204 measures the inhaled volume and the inspiratory pressure at the beginning of each breath in order to estimate the patient's compliance. For example, at the beginning of each breath, the ventilator retrieves data regarding the end-inspiratory pressure (EIP), the end-expiratory pressure (EEP), and the delivered volume associated with the last breath cycle. Delivered volume is determined based on integrating the net flow during the last inspiration and applying various volume compensations (e.g., tube compliance). Next, for example, the ventilator may utilize the retrieved data, the received tidal volume, and the patient's ideal body weight (IBW) and/or other monitored data to estimate patient compliance and calculates a revised effective pressure for use in the next breathing cycle that is projected to deliver the received tidal volume. The patient's compliance is put into an algorithm to calculate the amount of inspiratory pressure necessary for the next breath in order to deliver the received tidal volume. Alternative embodiments of how the calculate operation 204 calculates the inspiratory pressure to be delivered are also possible and any suitable method may be used. As another example, the percentage difference between the delivered and set tidal volumes may be calculated and the previously delivered pressure may be adjusted based on that difference.

The measurements allow the ventilator to determine the amount of tidal volume pulled by the patient at the beginning of the previous breath. If amount of tidal volume pulled by the patient is more than the received tidal volume, the ventilator calculates a lower inspiration pressure. If amount of tidal volume pulled by the patient is less than the received tidal volume, the ventilator calculates a higher inspiration pressure. Accordingly, the VCI breath type provides the patient with the received tidal volume by adjusting the provided pressure support in the next or following breath. Based on the amount of tidal volume pulled by the patient at the previous pressure, the ventilator in the calculate operation 204 determines the necessary amount of inspiration pressure ($P_i$) to achieve the received tidal volume during the next inspiration by the patient.

Method 200 includes a compare operation 206. The ventilator during compare operation 206 compares the calculated $P_i$ to a received minimum pressure ($P_{MIN}$). The $P_{MIN}$ setting is the minimum amount of pressure the ventilator must provide during inspiration. The received $P_{MIN}$ may be operator selected, input, or determined by the ventilator. In some embodiments, the ventilator may derive the $P_{MIN}$ based on other ventilator or patient parameters, or may have a stored default value for $P_{MIN}$ when $P_{MIN}$ is not selected or input by the operator. In some embodiments, the ventilator during compare operation 206 further compares the calculated $P_i$ to a received maximum pressure ($P_{MAX}$). The $P_{MAX}$ setting is the maximum amount of pressure the ventilator is allowed to provide during inspiration. The received $P_{MAX}$ may be operator selected, input, a default value, a value determined from some other parameter such as the patient's age, sex, body weight, ideal body weight, lung compliance, etc. or as otherwise determined by the ventilator. In some embodiments, the ventilator may derive the $P_{MAX}$ based on other parameters, such as $P_{MIN}$, or may have a stored default value for $P_{MAX}$ when $P_{MAX}$ is not selected or input by the operator.

Next, method 200 includes a minimum determination operation 208. The ventilator during the minimum determination operation 208 determines if the calculated $P_i$ is greater than the $P_{MIN}$. If the ventilator determines during the minimum determination operation 208 that the calculated $P_i$ is less than the $P_{MIN}$, then the ventilator performs a $P_{MIN}$ delivery operation 210. If the ventilator determines during the minimum determination operation 208 that the calculated $P_i$ is at least the $P_{MIN}$, then the ventilator performs the $P_i$ delivery operation 214.

In some embodiments, if the ventilator determines during the minimum determination operation 208 that the calculated $P_i$ is at least the $K_{IN}$, then the ventilator performs a $P_{MAX}$ determination operation 212 instead of the $P_i$ delivery operation 214. During the $P_{MAX}$ determination operation 212, the ventilator determines if the calculated $P_i$ is greater than the $P_{MAX}$. If the ventilator determines during the maximum determination operation 212 that the calculated $P_i$ is at least the $P_{MAX}$, then the ventilator performs a $P_{MAX}$ delivery operation 216. If the ventilator determines during the maximum determination operation 212 that the calculated $P_i$ is less than the $P_{MAX}$, then the ventilator performs the $P_i$ delivery operation 214.

As discussed above, method 200 includes the $P_{MIN}$ delivery operation 210. The ventilator during the $P_{MIN}$ delivery operation 210 delivers an inspiration pressure at the received $P_{MIN}$ setting. For example, if $P_{MIN}$ was set to 25 cm $H_2O$, the ventilator in the $P_{MIN}$ delivery operation 210 would deliver an inspiration pressure of 25 cm $H_2O$. The $P_{MIN}$ setting may be set automatically by the ventilator based on ventilator or patient parameters, may be a stored default value, or may be input or selected by the operator. The received $P_{MIN}$ prevents the $P_i$ from falling to a minimum of 5, which may happen in a VC+ breath type. This minimum pressure is beneficial in weak patients that need a minimum level of pressure support to promote adequate gas exchange in the lungs and support a reasonable amount of work for the patient in the acute lung injury state. After the performance of the $P_{MIN}$ delivery operation 210, the ventilator performs exhalation operation 218.

Method 200 further includes the $P_i$ delivery operation 214. The ventilator during the $P_i$ delivery operation 214 delivers the calculated $P_i$ determined by the ventilator in the calculate operation 204. For example, if the ventilator in the calculate operation 204 calculates a $P_i$ of 28 cm $H_2O$, the ventilator during the $P_i$ delivery operation 214 delivers 28 cm $H_2O$ of inspiration pressure. After the performance of the $P_{MIN}$ delivery operation 210, the ventilator performs exhalation operation 218.

In some embodiments, method 200 further includes the $P_{MAX}$ delivery operation 216. The ventilator during the $P_{MAX}$ delivery operation 216 delivers an inspiration pressure at the received $P_{MAX}$ setting. For example, if $P_{MAX}$ was set to 35 cm $H_2O$, the ventilator in the $P_{MAX}$ delivery operation 210 would deliver an inspiration pressure of 35 cm $H_2O$. The $P_{MAX}$ setting may be set automatically by the ventilator based on ventilator or patient parameters, may be stored default valued, or may be input or selected by the operator. The received $P_{MAX}$ prevents the $P_i$ from increasing to a level that could cause damage to the lungs, such as barotrauma. After the performance of the $P_{MIN}$ delivery operation 210, the ventilator performs exhalation operation 218.

As discussed above, method 200 includes an exhalation operation 218. The ventilator during the exhalation operation 218, triggers and executes an exhalation by the patient. The transition between inspiration to exhalation may be synchronized to a patient's spontaneous breathing efforts and/or to the ventilator-controlled breaths. For example, when the set inhalation time is reached the ventilator initiates exhalation regardless of actual tidal volume delivered in that breath. Exhalation lasts from the end of inspiration until the beginning of the next inspiration. For instance, in a non-triggering patient, the exhalation time ($T_E$) is based on at least two of a received respiration rate, a received inhalation time, a received expiration time, or a received I:E ratio.

Upon the end of exhalation, another mandatory breath is given to the patient. At the end of exhalation or at the beginning of the next mandatory breath the ventilator repeats at least a portion of method 200. As illustrated in FIG. 2, the ventilator performs calculate operation 204 at the beginning of the next mandatory breath followed by the following steps of method 200. Alternatively, if the ventilator received new parameters, such as a new tidal volume, the ventilator performs receive operation 202 at the beginning of the next mandatory breath followed by the following steps of method 200. Accordingly, at least a portion of method 200 is performed for each mandatory breath given by the ventilator during method 200.

In some embodiments, the ventilator during method 200 may detect patient initiated triggers above the given $P_i$ and PEEP during inspiration and exhalation based on received sensor data and information similar to the BL breath type, which allows and tracks patient triggered spontaneous inspirations above the given $PEEP_H$ and $PEEP_L$. In these embodiments, the ventilator allows the patient to pull additional volume above what is provided at $P_i$ and PEEP based on detected patient initiated triggers. In further embodiments, the ventilator during method 200 may track each patient initiated trigger, including, number, duration, volume, pressure, etc. However, the ventilator during method 200 does not utilize this information in the calculation of the next $P_i$ during calculation operation 204. Accordingly, during these embodiments, the ventilator during method 200 calculates the $P_i$ for the next inhalation based solely on the amount of tidal volume taken by the patient during the delivery of the previous $P_i$ for the initiation of inhalation during calculation operation 204.

In further embodiments, the ventilator during method 200 provides pressure support to any detected patient initiated breaths above the delivered PEEP and $P_i$ based on a received pressure support ($P_{SUPP}$) setting. The $P_{SUPP}$ setting may be any parameter for providing additional pressure as known by a person of skill in the art for ventilating a patient. For example, the $P_{SUPP}$ may vary based on the amount of volume pulled by the patient or may be a set amount or percent of pressure that is given regardless of the amount of volume pulled by the patient. In some embodiments, $P_{SUPP}$ is limited by $P_{MAX}$. In these embodiments, the $P_{SUPP}$ will not provide a pressure that is greater than $P_{MAX}$. In some embodiments, $P_{SUPP}$ is not limited by $P_{MAX}$. In these embodiments, the $P_{SUPP}$ provided may exceed a received $P_{MAX}$.

Any suitable type of triggering detection for determining a patient trigger may be utilized by the ventilation system, such as nasal detection, diaphragm detection, and/or brain signal detection. Further, patient triggering may be detected via a pressure-monitoring method, a flow-monitoring method, direct or indirect measurement of neuromuscular signals, or any other suitable method. Sensors suitable for this detection may include any suitable sensing device as known by a person of skill in the art for a ventilator.

In some embodiments, the ventilator during method 200 executes an alarm when the received tidal volume is not delivered to the patient. In some embodiments, the ventilator during method 200 executes an alarm when the inspired volume of the patient is above a predetermined threshold. These parameters are also tracked and alarm if above predetermined thresholds during a VC+ breath type. The term "alarm" as used herein includes any suitable visual, audio, and/or vibrational notification. Further, the term "alarm" as used herein further includes sent messages, such as emails, SMS text messages, and/or other transmitted notifications.

In one embodiment, the steps of method 200 are performed by a computer-readable medium having computer-executable instructions. In another embodiment, the ventilator system includes means for performing the steps of method 200. The means for performing the steps of method 200 are disclosed above, such as in ventilator 100.

In another embodiment, the ventilator system includes means for receiving a tidal volume and a PEEP; means for receiving a minimum inspiration pressure; means for receiving at least two of an inspiration time, an exhalation time, an I:E ratio, and a respiratory rate; means for calculating a calculated pressure based on measurements taken from a previous inspiration indicative of tidal volume delivered to the patient; means for comparing the calculated pressure to the received minimum inspiration pressure; means for delivering a delivered inspiration pressure during a next inhalation to the patient, the delivered inspiration pressure determined based on the step of comparing the calculated pressure to the received minimum inspiration pressure; and means for delivering, after the next inhalation, the received PEEP

EXAMPLE 1

Figure 3:
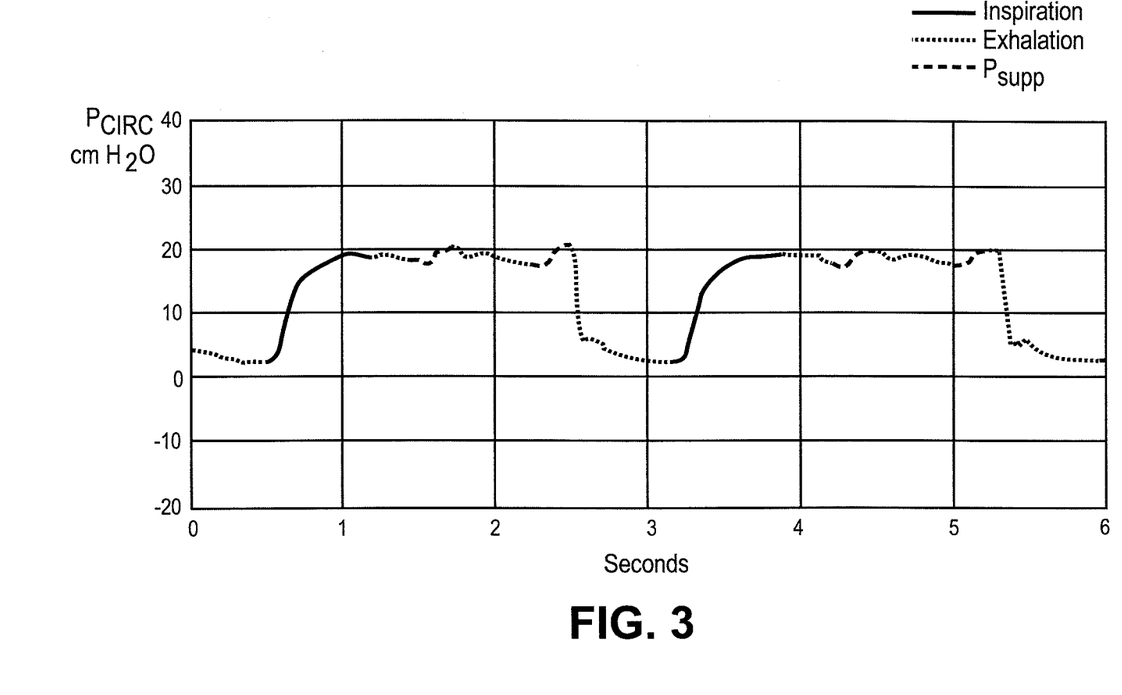
FIG. 3 illustrates an embodiment of a pressure waveform showing changes from inspiration to expiration during a VIC breath type.

FIG. 3 illustrates an embodiment of a pressure waveform showing changes from inspiration to exhalation during a VCI breath type. During inspiration, the pressure waveform illustrates the amount of pressure delivered during the initial inspiration based on solid line segment. Exhalation to the received PEEP is shown by a dotted line segment in FIG. 3. During inspiration and exhalation any additional pressure support provided in response to a detected spontaneous breath is designated by a dashed line segment.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various embodiments have been described for purposes of this disclosure, various changes and modifications may be made which are well within the scope of the present invention. Numerous other changes may be made which will readily suggest themselves to those skilled in the art and which are encompassed in the spirit of the disclosure and as defined in the appended claims.

What is claimed is:

1. A method for ventilating a patient with a ventilator comprising:
receiving a target tidal volume and a set positive end expiratory pressure (PEEP) by a ventilator;
receiving a set minimum inspiration pressure by the ventilator;
receiving at least two of a set inspiration time, a set exhalation time, a set inspiration time to expiration time ratio (I:E ratio), and a set respiratory rate by the ventilator;
delivering a first inspiration pressure to a patient in a first breath;
calculating a revised effective pressure for delivery to the patient to achieve the target tidal volume based on measurements taken from the first breath indicative of a tidal volume delivered to the patient in the first breath;
comparing the calculated revised effective pressure to the received set minimum inspiration pressure;
delivering a second inspiration pressure with the ventilator during a second breath to the patient, the second inspiration pressure is determined based on the calculated revised effective pressure and the step of comparing the calculated revised effective pressure to the received set minimum inspiration pressure;
delivering the PEEP during exhalation with the ventilator;
delivering an I:E ratio of greater than 4:1 during each breath without requiring a clinician to enter both a set $PEEP_{HIGH}$ setting and a set $PEEP_{LOW}$ setting; and delivering a spontaneous breath in response to a patient initiated trigger during inspiration above the delivered second inspiration pressure and during expiration above the delivered PEEP.

2. The method of claim 1, wherein the step of comparing the calculated revised effective pressure to the received set minimum inspiration pressure includes determining that the calculated revised effective pressure is less than the received set minimum inspiration pressure, and
wherein the-delivered second inspiration pressure is the received set minimum inspiration pressure.

3. The method of claim 1, wherein the step of comparing the calculated pressure to the received minimum inspiration pressure includes determining that the calculated pressure is more than the received minimum inspiration pressure, and
wherein the delivered second inspiration pressure is the calculated revised effective pressure.

4. The method of claim 1, further comprising receiving at least one of a set rise time and a set $FiO_2$ by the ventilator.

5. The method of claim 1, further comprising receiving a set pressure support setting that is applied to the spontaneous breath delivered by the ventilator during inspiration above the delivered second inspiration pressure and during expiration above the delivered PEEP.

6. The method of claim 1, further comprising tracking the spontaneous breath delivered by the ventilator during inspiration above the delivered second inspiration pressure and during expiration above the delivered PEEP.

7. The method of claim 1, further comprising:
receiving a set maximum inspiration pressure by the ventilator; and
comparing the set maximum inspiration pressure-to the calculated revised effective pressure.

8. The method of claim 7, wherein the step of comparing the calculated revised effective pressure to the set maximum inspiration pressure includes determining that the calculated revised effective pressure is less than the set maximum inspiration pressure, and
wherein the delivered second inspiration pressure is the calculated revised effective pressure.

9. The method of claim 7, further comprising:
wherein the step of comparing the calculated revised effective pressure to the set maximum inspiration pressure includes determining that the calculated revised effective pressure is more than the set maximum inspiration pressure, and
wherein the delivered-second inspiration pressure is the set maximum inspiration pressure.

10. The method of claim 7, wherein the set maximum inspiration pressure is calculated based on the set minimum inspiration pressure.

11. The method of claim 7, further comprising:
receiving the set minimum inspiration pressure by the ventilator from a default minimum inspiration pressure setting in the ventilator; and
receiving the set maximum inspiration pressure by the ventilator from a default maximum inspiration setting in the ventilator.

12. The method of claim 1, further comprising:
receiving the set minimum inspiration pressure by the ventilator from a default minimum inspiration pressure setting in the ventilator.

13. The method of claim 1, further comprising:
receiving the set PEEP by the ventilator from a default PEEP setting in the ventilator.

14. The method of claim 1, further comprising:
executing an alarm when the tidal volume is not equivalent to the target tidal volume.

15. The method of claim 1, further comprising:
executing an alarm when the tidal volume of the patient is above a predetermined threshold.

16. A ventilator system comprising:
a pressure generating system adapted to generate a flow of breathing gas;
a ventilation tubing system including a patient interface for connecting the pressure generating system to a patient;
one or more sensors operatively coupled to at least one of the pressure generating system, the patient, and the ventilation tubing system, wherein at least one sensor is capable of generating an output indicative of an inspiration flow; and
a volume-targeted minimum pressure-control (VCI) module that calculates an inspiration pressure to achieve a target tidal volume when delivered to the patient based on a measured tidal volume from a previously delivered breath calculated from the output indicative of the inspiration flow, compares the calculated inspiration pressure to a set minimum pressure, and causes the pressure generating system to deliver in a following breath at least one of the calculated inspiration pressure and the set minimum pressure to the patient during inhalation based on the comparison of the calculated inspiration pressure to the set minimum pressure, and wherein the VCI module delivers an inspiration time to expiration time ratio (I:E ratio) of greater than 4:1 during each breath without requiring a clinician to enter both a set $PEEP_{HIGH}$ setting and a set $PEEP_{LOW}$ setting.

17. A computer-readable medium having non-transitory computer-executable instructions for performing a method of ventilating a patient with a ventilator, the method comprising:
repeatedly receiving a target tidal volume and a set positive end expiratory pressure (PEEP) by a ventilator;
repeatedly receiving a set minimum inspiration pressure by the ventilator;
repeatedly receiving at least two of a set inspiration time, a set exhalation time, a set inspiration time to expiration time ratio (I:E ratio), and a set respiratory rate by the ventilator;
repeatedly delivering a first inspiration pressure to a patient in a first breath;
repeatedly calculating a revised effective pressure for delivery to the patient to achieve the target tidal volume based on measurements taken from the first breath indicative of a tidal volume delivered to the patient in the first breath;
repeatedly comparing the calculated revised effective pressure to the received set minimum inspiration pressure;
repeatedly delivering a second inspiration pressure with the ventilator during a second breath to the patient, the second inspiration pressure is determined based on the calculated revised effective pressure and the step of comparing the calculated revised effective pressure to the received set minimum inspiration pressure;
repeatedly delivering, the set PEEP during exhalation with the ventilator;
repeatedly delivering an I:E ratio of greater than 4:1 during each breath without requiring a clinician to enter both a set $PEEP_{HIGH}$ setting and set $PEEP_{LOW}$ setting; and
repeatedly delivering a spontaneous breath in response to a patient initiated trigger during inspiration above the delivered second inspiration pressure and during expiration above the delivered PEEP.

* * * * *